US011185503B2

(12) United States Patent
Yim et al.

(10) Patent No.: US 11,185,503 B2
(45) Date of Patent: Nov. 30, 2021

(54) STABLE LIQUID COMPOSITION COMPRISING BOTULINUM TOXIN

(71) Applicant: DAEWOONG CO., LTD., Gyeonggi-do (KR)

(72) Inventors: Hyeona Yim, Gyeonggi-do (KR); Cheong-Sei Kim, Seoul (KR)

(73) Assignee: DAEWOONG CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/477,889

(22) PCT Filed: Oct. 17, 2017

(86) PCT No.: PCT/KR2017/011438
§ 371 (c)(1),
(2) Date: Jul. 14, 2019

(87) PCT Pub. No.: WO2018/135722
PCT Pub. Date: Jul. 26, 2018

(65) Prior Publication Data
US 2020/0121599 A1 Apr. 23, 2020

(30) Foreign Application Priority Data
Jan. 20, 2017 (KR) ........................ 10-2017-0009727

(51) Int. Cl.
A61K 9/08 (2006.01)
A61K 38/48 (2006.01)
A61K 9/00 (2006.01)
A61K 47/18 (2017.01)
A61K 47/38 (2006.01)
A61K 47/36 (2006.01)
A61K 47/26 (2006.01)

(52) U.S. Cl.
CPC .............. A61K 9/08 (2013.01); A61K 9/0019 (2013.01); A61K 38/4893 (2013.01); A61K 47/183 (2013.01); A61K 47/26 (2013.01); A61K 47/38 (2013.01)

(58) Field of Classification Search
CPC ...................................................... A61K 9/08
See application file for complete search history.

(56) References Cited

U.S. PATENT DOCUMENTS

| | | | |
|---|---|---|---|
| 5,811,096 A | 12/1998 | Aleman et al. | |
| 2010/0330123 A1 | 12/2010 | Thompson et al. | |
| 2012/0207787 A1* | 8/2012 | Hunt ...................... | A61K 47/32 424/239.1 |
| 2012/0238504 A1 | 9/2012 | Moyer et al. | |
| 2014/0302008 A1 | 10/2014 | Moyer et al. | |
| 2015/0064166 A1 | 3/2015 | Jung et al. | |
| 2015/0328293 A1 | 11/2015 | Webb et al. | |

FOREIGN PATENT DOCUMENTS

| | | |
|---|---|---|
| AU | 2016202526 A1 | 5/2016 |
| CN | 101687046 A | 3/2010 |
| CN | 102387791 A | 3/2012 |
| CN | 102869373 A | 1/2013 |
| CN | 101687046 A | 3/2021 |
| JP | 2010532784 A | 10/2010 |
| JP | 2012531442 A | 12/2012 |
| JP | 2015178505 A | 10/2015 |
| KR | 1020050084932 A | 8/2005 |
| KR | 1020090005963 A | 1/2009 |
| KR | 1020120102569 A | 9/2012 |
| KR | 1020160113597 A | 9/2016 |
| KR | 1017449000000 B1 | 6/2017 |
| NZ | 509349 A | 8/2003 |
| RU | 2220163 C1 | 12/2003 |
| WO | 2009008595 A1 | 1/2009 |
| WO | WO2010/090677 * | 8/2010 |
| WO | WO2010090677 A1 | 8/2010 |
| WO | 2010118888 A1 | 10/2010 |
| WO | 2010151840 A2 | 12/2010 |
| WO | WO2014004578 A1 | 1/2014 |
| WO | WO2017179775 A1 | 10/2017 |

OTHER PUBLICATIONS

New World Encyclopedia (Alanine). Oct. (Year: 2007).*
Schantz, E., et al., "Properties and Use of Botulinum Toxin and Other Microbial Neurotoxins in Medicine", "Microbiological Reviewss", 1992, pp. 80-99, vol. 56, No. 1, Publisher: American Society for Microbiology.
Sugiyama, H., "Clostridium botulinum Neurotoxin", "Microbiological Reviews", Sep. 1980, pp. 419-448, vol. 44, No. 3.
Pickett, A., "Botulinum Toxin as a Clinical Product: Manufacture and Pharmacology", "Clinical Applications of Botulinum Neurotoxin, Chapter 2", 2014, pp. 7-49.
"15. Amino Acids, Proteins and Nucleic Acids", Organic Chemistry (2nd Ed), Jul. 31, 2007, pp. 281-284, Publisher: China Agriculture Press.
"15. Amino Acids, Proteins and Nucleic Acids", Organic Chemistry (2nd Edition), Jul. 31, 2007, pp. 281-284, Eng Trans, Publisher: China Agriculture Press.
Office Action in Chinese Patent Application 201780086961.0, dated Jul. 12, 2021.

(Continued)

Primary Examiner — Sarah Alawadi
(74) Attorney, Agent, or Firm — Hultquist, PLLC; Steven J. Hultquist

(57) ABSTRACT

A stable liquid composition comprising a botulinum toxin as an active ingredient is described, which is ready-to-use without the need for a reconstitution process, and thus, it is possible to improve user's convenience, and reduce a deviation of botulinum toxin activity due to dilution errors in the reconstitution process. Further, the liquid composition efficiently prevents the botulinum toxin from aggregating even at a low botulinum toxin concentration to thereby have extremely excellent storage stability, and efficiently prevents adsorption of the botulinum toxin to a container, thereby constantly maintaining an activity of the botulinum toxin for each batch or for each liquid vial.

7 Claims, No Drawings

(56) References Cited

OTHER PUBLICATIONS

Office Action in Chinese Patent Application No. 201780086961.0, Jul. 12, 2021, Eng Trans.
"Non-polar Neutral Amino Acids", Biochemistry, Jul. 31, 2015, pp. 7-11, Publisher: China Press of Traditional Chinese Medicine.
"Non-polar Neutral Amino Acids", Biochemistry, Jul. 31, 2015, pp. 7-11, Eng Trans, Publisher: China Press of Traditional Chinese Medicine.

* cited by examiner

STABLE LIQUID COMPOSITION COMPRISING BOTULINUM TOXIN

CROSS-REFERENCE TO RELATED APPLICATIONS

This is a U.S. national phase under the provisions of 35 U.S.C. § 371 of International Patent Application No. PCT/KR17/11438 filed Oct. 17, 2017, which in turn claims priority under 35 U.S.C. § 119 of Korean Patent Application No. 10-2017-0009727 filed Jan. 20, 2017. The disclosures of International Patent Application No. PCT/KR17/11438 and Korean Patent Application No. 10-2017-0009727 are hereby incorporated herein by reference in their respective entireties, for all purposes.

TECHNICAL FIELD

The present disclosure relates to a stable liquid composition comprising a botulinum toxin as an active ingredient which is ready-to-use without the need for a reconstitution process, and particularly, to a liquid composition capable of preventing the botulinum toxin from aggregating even when the botulinum toxin is comprised at a low concentration to thereby exhibit high stability, and efficiently preventing adsorption, etc., to a container, to constantly maintain an activity of the botulinum toxin for each batch or for each liquid vial.

Specifically, the present disclosure relates to the liquid composition comprising (i) a botulinum toxin as an active ingredient, (ii) L-alanine or methyl cellulose, (iii) a non-ionic surfactant, and (iv) a buffer, and optionally, an isotonic agent.

Further, the present disclosure relates to a method for stabilizing a botulinum toxin using a liquid composition, the liquid composition comprising (i) a botulinum toxin, (ii) L-alanine or methyl cellulose, (iii) a non-ionic surfactant, and (iv) a buffer, and optionally, an isotonic agent.

BACKGROUND ART

A variety of *Clostridium* genus strains that secrete neurotoxic toxins have been discovered since the 1890s, and characteristics of toxins secreted by these strains have been identified for the last 70 years (Schant, E. J. et al., *Microbiol. Rev.*, 56:80, 1992).

The toxin having neurotoxicity derived from the *Clostridium* genus strains, i.e., the botulinum toxin is classified into 7 types from types A to G according to serological characteristics thereof. Each toxin has about 150 kDa of toxin protein, which is naturally composed of complexes that are combined with several non-toxic proteins. A medium complex (300 kDa) is composed of a toxin protein and a non-toxic non-hemagglutinin protein, and a large complex (450 kDa) and a large-large complex (900 kDa) have forms in which the intermediate complexes are combined with hemagglutinin (Sugiyama, H., *Microbiol. Rev.*, 44: 419, 1980). These non-toxic non-hemagglutinin proteins are known to protect toxins from low pH and various proteases in the intestine.

In particular, it has been found that when the botulinum toxin type A is administered locally at a dosage that does not affect a human body systemically, it is possible to paralyze localized muscles of locally administered sites, wherein the characteristic is widely usable for wrinkle removal, therapeutic uses of stiffness hemiplegia and cerebral palsy, etc., and thus, the demand has been growing rapidly.

Meanwhile, a ready-to-use form of liquid composition comprising a botulinum toxin as an active ingredient without performing a reconstitution process is preferable in view of user's convenience, but the botulinum toxin has a disadvantage in that stability of the botulinum toxin is greatly reduced in a liquid form, and thus, in order to increase the stability of the protein, conventional commercial botulinum toxin preparations are prepared in a lyophilized form or in a dry powder form which is vacuum-dried.

However, the dry powder formulations prepared by lyophilization, etc., have problems in that since the reconstitution process is required to be performed during use, it is inconvenient when used, and deviation of botulinum toxin amount to be administered, particularly, deviation in view of an activity, etc., occur due to errors of a dilution process in the reconstitution process, etc. Thus, there is a growing demand for a liquid composition capable of improving user's convenience, and minimizing errors in the reconstitution process.

In particular, since the botulinum toxin is highly toxic, a trace amount should be administered for therapeutic or cosmetic purpose, and thus, the liquid composition of a botulinum toxin at a lower concentration than a liquid composition of a high concentration botulinum toxin is preferred.

However, it is known that when the botulinum toxin is present at a low concentration, it tends to be aggregated to each other, and be adsorbed to a container, and thus, desired and sufficient activity of the botulinum toxin is not exhibited or rather the activity of the toxin becomes higher, etc., that is, activity deviation of the botulinum toxin occurs for each batch or for each liquid vial, which causes unexpected side effects, and the like, and consequently, it is not easy to prepare a stabilized liquid composition having a low botulinum toxin concentration.

In this aspect, there is an urgent need for a novel form of a liquid composition capable of improving convenience when used by a user, efficiently preventing a botulinum toxin from aggregating even at a low botulinum toxin concentration, efficiently preventing the botulinum toxin from being adsorbed to a container to constantly maintain an activity of the botulinum toxin for each batch or for each liquid vial.

DISCLOSURE

Technical Problem

An object of the present disclosure is to provide a novel form of a liquid composition capable of efficiently preventing a botulinum toxin from aggregating even at a low botulinum toxin concentration, efficiently preventing the botulinum toxin from being adsorbed to a container to thereby constantly maintain an activity of the botulinum toxin for each batch or for each liquid vial.

Technical Solution

In order to achieve the foregoing objects, the present disclosure provides a stable liquid composition of a botulinum toxin comprising (i) a botulinum toxin as an active ingredient, (ii) L-alanine or methyl cellulose, (iii) a non-ionic surfactant, and (iv) a buffer, and optionally, an isotonic agent.

Further, the present disclosure also provides a method for stabilizing a botulinum toxin using a liquid composition, the liquid composition comprising (i) a botulinum toxin, (ii)

L-alanine or methyl cellulose, (iii) a non-ionic surfactant, and (iv) a buffer, and optionally, an isotonic agent.

BEST MODE

Unless defined otherwise, all the technical and scientific terms used herein have the same meanings as those generally understood by persons skilled in the art to which the present disclosure pertains. In general, the nomenclature used in the present specification is well known in technical fields and generally used.

In an aspect, the present disclosure relates to a liquid composition comprising (i) a botulinum toxin as an active ingredient, (ii) L-alanine or methyl cellulose, (iii) a non-ionic surfactant, and (iv) a buffer, and optionally, an isotonic agent.

In the present disclosure, the term "botulinum toxin" is used to encompass both neurotoxins (NTXs) produced by *Clostridium botulinum* strains or mutants thereof and modified, recombinant, hybrid, and chimeric botulinum toxins.

The recombinant botulinum toxin may have a light chain and/or a heavy chain recombinantly produced by non-*Clostridium* species. Further, the botulinum toxin of the present disclosure encompasses botulinum toxin serotypes A, B, C, D, E, F, and G, and encompasses both not only botulinum toxin complexes (i.e., 300, 600 and 900 kDa complexes) but also pure botulinum toxin (i.e., about 150 kDa neurotoxic molecule), both of which are useful in the practice of the present disclosure.

Preferably, the botulinum toxin contained in the liquid composition of the present disclosure is a botulinum toxin type A.

The liquid composition according to the present disclosure may contain the botulinum toxin in a content of about 10 to 200 unit/ml or about 20 to 150 unit/ml, preferably about 25 to 100 unit/ml, or 25 to 75 unit/ml, and the most preferably 25 to 50 unit/ml, but the content of the botulinum toxin is not limited thereto.

The liquid composition of the botulinum toxin according to the present disclosure imparts hydrophobicity using L-alanine or methyl cellulose which is a kind of non-polar amino acid. The L-alanine may increase solubility of the botulinum toxin through a hydrophobic effect or a salt effect, and may adjust a critical micelle concentration when used in combination with a non-ionic surfactant, in particular, polysorbate 20 or polysorbate 80. The methyl cellulose is a polymer that has similar amphipathic property to polysorbate 20 or polysorbate 80, but has temperature sensitivity in a different form of surfactant, which is expected to contribute to thermal stability.

In the liquid composition of the botulinum toxin according to the present disclosure, the L-alanine may have a content of 0.01 to 1% (w/v), preferably 0.05 to 0.5% (w/v), and the most preferably 0.075 to 0.3% (w/v) based on the total content of the composition. In an exemplary embodiment, the L-alanine may have a content of 0.1% (w/v) based on the total content of the composition.

In the liquid composition of the botulinum toxin according to the present disclosure, the methyl cellulose may have a content of 0.00001 to 0.1% (w/v), preferably 0.0001 to 0.01% (w/v), and the most preferably 0.0005 to 0.0015% (w/v) based on the total content of the composition. In an exemplary embodiment, the methyl cellulose may have a content of 0.00125 or 0.000625% (w/v) based on the total content of the composition.

In the liquid composition of the botulinum toxin of the present disclosure, the non-ionic surfactant may be polysorbate 20 or polysorbate 80, but is not limited thereto. Preferably, polysorbate 20 may be used. It is found that the non-ionic surfactant, in particular, polysorbate 20, is used to prevent the botulinum toxin from being adsorbed to a container, and greatly increases stability of the botulinum toxin while simultaneously improving hydrophobicity and surface interaction, and preventing adsorption to the container. However, when polysorbate 20 or polysorbate 80 is included in the liquid composition, the botulinum toxin may be simultaneously stabilized, but there is a problem in that an activity of the botulinum toxin may be higher than a desired value.

In order to solve this problem, in the present disclosure, it is found that when polysorbate 20 or polysorbate 80 is used in a trace amount ranging from 0.00001 to 0.1% (w/v), preferably 0.0001 to 0.01% (w/v), and the most preferably, 0.0005 to 0.0015% (w/v) based on the total content of the composition, the problem that the activity of the botulinum toxin is high may be prevented, and adsorption to the container may be effectively prevented to constantly maintain an activity of the botulinum toxin for each batch or for each liquid vial. In an exemplary embodiment, the content of polysorbate 20 is 0.001% (w/v) based on the total content of the composition.

The liquid composition of the botulinum toxin of the present disclosure may contain a physiologically compatible buffer to maintain the pH below an isoelectric point, thereby securing long-term stability. The physiologically compatible buffer is required to be capable of maintaining the pH in the range of 4.5 to 6.5, preferably in the range of 5.0 to 6.0, and the most preferably about 5.5. As the physiologically suitable buffer, sodium citrate, succinic acid, phosphoric acid, potassium monophosphate, sodium acetate, sodium chloride, etc., may be used. Preferably, sodium citrate may be used as the buffer in the liquid composition according to the present disclosure. The sodium citrate buffer is capable of controlling pH change that has a serious effect on stability at the time of long-term storage of protein drugs, but has a possibility of decrease in content and activity (potency) when used in combination with specific excipients, and thus, the use of the sodium citrate buffer needs to be determined by conducting a compatibility test.

The physiologically compatible buffer in the liquid composition of the botulinum toxin of the present disclosure may have a content of 5 to 35 mM, preferably 10 to 30 mM, and the most preferably 15 to 25 mM based on the total content of the composition. In an exemplary embodiment, sodium citrate at pH 5.5 is contained as the physiologically compatible buffer in the content of 20 mM based on the total content of the composition. The combination of L-alanine and sodium citrate buffer was found to significantly increase the stability of botulinum toxin type A.

Further, the liquid composition of the botulinum toxin of the present disclosure may optionally further comprise as an isotonic agent. Examples of the isotonic agent may comprise sodium chloride, glycerin, mannitol, sucrose, potassium chloride, dextrose, etc. The content of the isotonic agent may be 0.7 to 0.95% (w/v) based on the total content of the composition. Preferably, the liquid composition of the botulinum toxin of the present disclosure comprises 0.7 to 0.95% (w/v), and the most preferably 0.9% (w/v) sodium chloride as the isotonic agent.

In an exemplary embodiment, the liquid composition of the botulinum toxin of the present disclosure may contain 0.01 to 1% (w/v) alanine, 0.00001 to 0.1% (w/v) polysorbate 20 or polysorbate 80, 5 to 35 mM sodium citrate, and 0.7 to 0.95% (w/v) the isotonic agent based on the total content of the composition.

In another exemplary embodiment, a botulinum toxin type A liquid injection of the present disclosure may contain 0.00001 to 0.1% (w/v) methyl cellulose, 0.00001 to 0.1% (w/v) polysorbate 20 or polysorbate 80, 5 to 35 mM sodium citrate, and 0.7 to 0.95% (w/v) the isotonic agent based on the total content of the composition.

The liquid composition of the botulinum toxin of the present disclosure may be administered via conventional routes of administration. In some exemplary embodiments of the present disclosure, the liquid composition of the botulinum toxin is administered by intramuscular injection or subcutaneous injection, which is a method of topical administration, to a subject in need thereof. Since the liquid composition of the botulinum toxin of the present disclosure is in a liquid state, it is possible to be administered directly without performing a reconstitution step when used. In addition, the botulinum toxin included in the liquid composition of the botulinum toxin according to the present disclosure may maintain stability for about 12 weeks at room temperature or up to 5 weeks under stress conditions.

The stabilized liquid composition of the botulinum toxin of the present disclosure is usable for treatment of neuromuscular disorders characterized by a hyperactive skeletal muscle. Further, the liquid composition of the botulinum toxin of the present disclosure may be used for various purposes such as treatment of diseases and enhancement of beauty, etc., for headache, migraine, tension headache, sinus headache, cervical headache, sweating disorder, axillary hyperhidrosis, hand hyperhidrosis, foot hyperhidrosis, Frey's syndrome, hyperkinetic skin line, facial wrinkles, frown wrinkles, eye wrinkles, wrinkles near the mouth, nasolabial fold, skin disorder, achalasia, strabismus, chronic anal fissure, eyelid seizure, musculoskeletal pain, fibromyalgia, pancreatitis, tachycardia, prostate hypertrophy, prostatitis, urinary retention, urinary incontinence, irritable bladder, half-sided facial convulsion, tremor, muscle cramp, gastrointestinal disorder, diabetes, sialism, detrusor-sphincter cooperative disorder, post-stroke stiffness, wound recovery, pediatric cerebral palsy, smooth muscle spasm, restenosis, local dystonia, epilepsy, cervical dystonia, thyroid disorder, hypercalcemia, obsessive disorder, arthritis pain, Raynaud's syndrome, striae distensae, peritoneal adhesion, vasospasm, runny nose, muscle contracture, laryngeal dystonia, handwriting cramp, and carpal tunnel syndrome, etc.

In another aspect, the present disclosure relates to a method for stabilizing a botulinum toxin using a liquid composition, the liquid composition comprising (i) a botulinum toxin, (ii) L-alanine or methyl cellulose, (iii) a non-ionic surfactant, and (iv) a buffer, and optionally, an isotonic agent.

In an exemplary embodiment, the present disclosure relates to a method for stabilizing a botulinum toxin preparation comprising forming a liquid composition by combining (i) a botulinum toxin with (ii) L-alanine, (iii) polysorbate 20 or polysorbate 80, (iv) sodium citrate, and optionally sodium chloride which is an isotonic agent, wherein the alanine has a content of 0.01 to 1% (w/v), the polysorbate 20 or polysorbate 80 has a content of 0.00001 to 0.1% (w/v), the sodium citrate has a concentration of 5 to 35 mM, and the sodium chloride which is the isotonic agent has a content of 0.7 to 0.95% (w/v) based on the total content of the liquid composition.

In another exemplary embodiment, the present disclosure relates to a method for stabilizing a botulinum toxin preparation comprising forming a liquid composition by mixing (i) a botulinum toxin with (ii) methyl cellulose, (iii) polysorbate 20 or polysorbate 80, (iv) sodium citrate, and optionally sodium chloride which is an isotonic agent, wherein the methyl cellulose has a content of 0.00001 to 0.1 (w/v), the polysorbate 20 or polysorbate has a content of 0.00001 to 0.1% (w/v), the sodium citrate has a concentration of 5 to 35 mM, and the sodium chloride which is the isotonic agent has a content of 0.7 to 0.95% (w/v) based on the total liquid composition.

Since the botulinum toxin preparation stabilized by the method of the present disclosure is usable as an injection as it is as a liquid preparation, a separate reconstitution process is not necessary before use, and thus, the botulinum toxin preparation may be conveniently used, and may be stored in a stable state for about 6 months or more.

EXAMPLES

Hereinafter, the present disclosure will be described in more detail with reference to the following Examples. However, the following Examples are only for exemplifying the present disclosure, and it will be obvious to those skilled in the art that the scope of the present disclosure is not construed to be limited to these Examples.

Example 1: Evaluation of Content of Botulinum Toxin According to Types and Contents of Amphipathic Excipient In order to find an excipient suitable for enhancing the stability of botulinum toxin, various types of amphipathic excipients were added to *Clostridium botulinum* toxin type A, and then, effects of types and contents of the amphipathic excipients on the content of botulinum toxin were evaluated by ELISA test using Versamax microplate reader BC-138 and BC-378 (Molecular Devices, LLC). A sodium citrate buffer (hereinafter referred to as "SC buffer" or "SC buffer solution") and a sodium chloride buffer were used as buffers. Unless otherwise noted, the sodium citrate buffer prepared by comprising 0.9% (w/v) sodium chloride as an isotonic agent was used.

The botulinum toxin type A used in the test was prepared by the method described in Korean Patent No. 1,339,349.

For the ELISA test, botulinum toxin type A standards (Daewoong Pharmaceutical) diluted to various concentrations and a liquid composition according to the present disclosure were dispensed in a 96-well plate coated with botulinum type A antitoxin (NIBSC, 59/021), and the ELISA test was performed by using a Sandwich ELISA technique.

The respective standards and the liquid composition were subjected to primary and secondary antibody reactions, followed by reaction with a substrate. Then, an activity of the liquid composition according to a standard curve of the standard was measured by measuring absorbance at a wavelength of 450 to 540 nm. Hereinafter, other ELISA methods in the present disclosure were also tested by the same method, and the contents were calculated.

Test results were expressed by a percentage as compared to the control group (0.02% human serum albumin, 0.9% sodium chloride) added at the same stock concentration (2 ng/ml) as each composition. The excipient was added to each content shown in Table 1 to prepare 1 L of an excipient liquid, and then the botulinum toxin was added at a concentration of 40 U/ml, and the decreased content as compared to 40 U/ml was confirmed.

TABLE 1

Effects of types and contents of the amphipathic excipients on the content of botulinum toxin

| Batch No. | Amphipathic Excipients | Contents (w/v %) | Buffer | Concentration Ratio |
|---|---|---|---|---|
| 1 | PEG 400 | 5 | 0.9% NaCl | 2% |
| 2 | PEG 400 | 5 | S.C buffer (pH 5.5) | 11% |
| 3 | PEG 400 | 0.5 | 0.9% NaCl | 7% |
| 4 | PEG 400 | 0.5 | S.C buffer (pH 5.5) | 9% |
| 5 | PEG 400 | 0.05 | 0.9% NaCl | 3% |
| 6 | PEG 400 | 0.05 | S.C buffer (pH 5.5) | 8% |
| 7 | Methyl Cellulose | 0.05 | 0.9% NaCl | 117% |
| 8 | Methyl Cellulose | 0.05 | S.C buffer (pH 5.5) | 99% |
| 9 | Methyl Cellulose | 0.01 | 0.9% NaCl | 104% |
| 10 | Methyl Cellulose | 0.01 | S.C buffer (pH 5.5) | 103% |
| 11 | Methyl Cellulose | 0.002 | 0.9% NaCl | 81% |
| 12 | Methyl Cellulose | 0.002 | S.C buffer (pH 5.5) | 96% |
| 13 | sod. CMC | 0.1 | 0.9% NaCl | 10% |
| 14 | sod. CMC | 0.1 | S.C buffer (pH 5.5) | 24% |
| 15 | sod. CMC | 0.02 | 0.9% NaCl | 12% |
| 16 | sod. CMC | 0.02 | S.C buffer (pH 5.5) | 18% |
| 17 | sod. CMC | 0.004 | 0.9% NaCl | 15% |
| 18 | sod. CMC | 0.004 | S.C buffer (pH 5.5) | 17% |
| 19 | PVPK 17 | 1 | 0.9% NaCl | 46% |
| 20 | PVPK 17 | 1 | S.C buffer (pH 5.5) | 84% |
| 21 | PVPK 17 | 0.2 | 0.9% NaCl | 15% |
| 22 | PVPK 17 | 0.2 | S.C buffer (pH 5.5) | 74% |
| 23 | PVPK 17 | 0.04 | 0.9% NaCl | 66% |
| 24 | PVPK 17 | 0.04 | S.C buffer (pH 5.5) | 74% |
| 25 | Polysorbate 20 | 0.05 | 0.9% NaCl | 99% |
| 26 | Polysorbate 20 | 0.05 | S.C buffer (pH 5.5) | 93% |
| 27 | Polysorbate 20 | 0.01 | 0.9% NaCl | 93% |
| 28 | Polysorbate 20 | 0.01 | S.C buffer (pH 5.5) | 96% |
| 29 | Polysorbate 20 | 0.002 | 0.9% NaCl | 91% |
| 30 | Polysorbate 20 | 0.002 | S.C buffer (pH 5.5) | 101% |

As shown in Table 1, it was confirmed that when the methyl cellulose or polysorbate 20 was added, the activity of the botulinum toxin type A was maintained to be high. On the contrary, when PEG 400, sodium carboxymethyl cellulose (Sod. CMC) or povidone K17 (PVPK17) was added, the activity of the botulinum toxin type A was reduced.

Accordingly, in the present disclosure, methyl cellulose or polysorbate 20 was used as an amphipathic excipient to stabilize the botulinum toxin. Further, it could be confirmed that when the buffer, particularly, a sodium citrate buffer or a sodium chloride buffer was used together, a property in which an activity of the botulinum toxin type A is maintained, i.e., stability property was different.

Example 2: Other Excipient that is Usable in Combination with Polysorbate 20

The maximum available concentration of polysorbate 20 was confirmed, and an effect on the content of botulinum toxin when used in combination with other excipient while setting polysorbate 20 as a basic excipient was evaluated. Polysorbate 20 was selected as a primary excipient according to the results of Example 1, and screening for each excipient using the ELISA test method was performed.

As stabilizers that are expected to function together with the selected polysorbate 20, L-proline and L-alanine were added as candidate excipients in consideration of physical properties such as hydrophobicity, pKa, pKb value, and isoelectric point of the amino acid, etc. Since an additional stabilizer as well as polysorbate 20 is required to maintain structural stability of the protein, two amino acids, L-proline and L-alanine, were selected in consideration of pKa 6.0 of the botulinum toxin A.

An animal potency test was conducted by administering standard solutions in which the botulinum toxin type A in a dry powder form is diluted to various concentrations and the liquid composition according to the present disclosure into peritoneal cavity of 10 ICR-mice (4 weeks old, body weight: 18 to 22 g) (0.1 ml/mouse), respectively, and the number of dead animals and the number of surviving animals were confirmed for 3 days, and then, an activity was calculated using a statistical program (StatPlus® 2009 Program (Release 5.9.8, AnalystSoft)). Hereinafter, other animal potency tests in the present disclosure were also performed by the same method, and the activity was calculated.

TABLE 2

Results for combined use of polysorbate 20 with amino acids

| Batch No. | Excipient 1 | Content (w/v %) | Excipient 2 | Content (w/v %) | Buffer | ELISA | Animal potency Test |
|---|---|---|---|---|---|---|---|
| NBT-25I-L169 | L-alanine (25 mM) | 0.223 | polysorbate 20 | 0.5 | N/A | 117% | 143.8% |
| NBT-25I-L163 | L-alanine (25 mM) | 0.223 | polysorbate 20 | 1 | N/A | 79% | N/A |
| NBT-25I-L164 | L-alanine (25 mM) | 0.223 | polysorbate 20 | 2 | N/A | 48% | N/A |
| NBT-25I-L165 | L-proline (25 mM) | 0.29 | polysorbate 20 | 0.5 | N/A | 86% | N/A |
| NBT-25I-L166 | L-proline (25 mM) | 0.29 | polysorbate 20 | 1 | N/A | 65% | N/A |
| NBT-25I-L167 | L-proline (25 mM) | 0.29 | polysorbate 20 | 2 | N/A | 35% | N/A |

N/A; not application

When the amount of the botulinum toxin treated at a concentration of 40 U/ml was converted to 100%, and analyzed by ELISA method, the content of the botulinum toxin was decreased to 80% or less when the content of polysorbate 20 was 1% or more, showing the decrease in content. As a result of conducting an animal potency test using the test group NBT-25I-L169 which is the only group maintaining 100% content, the activity was 143.8% as compared to the 100% content value, and the activity was highly evaluated. Further, when polysorbate 20 was used in combination with L-alanine, an initial content value of the botulinum toxin type A was high in the ELISA test as compared to when polysorbate 20 was used in combination with L-proline, and thus, polysorbate 20 and L-alanine were used together in the present disclosure.

Example 3: Effect of Combination of Polysorbate 20 and L-Alanine on Potency

In order to confirm the effect of the polysorbate 20 and L-alanine which were selected through Example 2 on the activity (potency) of the botulinum toxin, polysorbate 20 and L-alanine were added together to prepare a botulinum toxin type A formulation as described below, and the effect on the activity (potency) thereof was confirmed.

TABLE 3

Results of measuring potency on combination of polysorbate 20 and L-alanine

| Batch No. | Excipient 1 | Content (w/v %) | Excipient 2 | Content (w/v %) | Animal potency (%) |
|---|---|---|---|---|---|
| NBTS 50I-T009 | polysorbate 20 | 0.015 | L-alanine | 0.01 | 120.7 |
| NBTS 50I-T010 | polysorbate 20 | 0.015 | L-alanine | 0.01 | 114.3 |
| NBTS 50I-T021 | polysorbate 20 | 0.1 | L-alanine | 0.1 | 201.4 |
| NBTS 50I-T022 | polysorbate 20 | 0.1 | L-alanine | 0.1 | 142 |
| NBTS 50I-T007 | polysorbate 20 | 0.1 | L-alanine | 0.2 | 148.2 |
| NBTS 50I-T008 | polysorbate 20 | 0.1 | L-alanine | 0.2 | 136.8 |

Table 3 shows that even through the same contents of polysorbate 20 and L-alanine were used under the same experimental conditions, the activity (potency) of the botulinum toxin type A was different for each batch, and the activity was overall highly evaluated. Overall, the high evaluation of the botulinum toxin activity of polysorbate 20 continues until the concentration of polysorbate 20 is up to 0.015%, indicating that the flow of values for each batch produced is not constant and unstable. Since this phenomenon was considered to be caused by polysorbate 20 having amphipathic property, it was confirmed that it was necessary to comprise polysorbate into the liquid composition in a content capable of maintaining the activity (potency) of the botulinum toxin constantly.

Example 4: Evaluation of Potency According to Content of Polysorbate 20

In order to investigate the effect of the content of polysorbate 20 on the potency of the botulinum toxin, an animal potency screening of the liquid formulation having the following composition was conducted by changing the contents. The animal potency tests of polysorbate 20 at various concentrations were conducted as described below in order to confirm whether the activity was highly evaluated according to the concentration of the polysorbate 20. 5 mM sodium citrate was used to compensate for a phenomenon that stability of protein is reduced by the decreased polysorbate 20.

TABLE 4

Results of measuring animal potency according to content of polysorbate 20

| Batch No. | L-alanine (w/v %) | polysorbate 20 (w/v %) | Buffer | Animal potency (w/v %) |
|---|---|---|---|---|
| NBTS-50-T078 | 0.1 | 0.0025 | 5 mM S.C buffer, pH 5.5 | 132.6 |
| NBTS-50-T079 | 0.1 | 0.001 | 5 mM S.C buffer, pH 5.5 | 121.1 |
| NBTS-50-T080 | 0.1 | 0.00075 | 5 mM S.C buffer, pH 5.5 | 114.4 |
| NBTS-50-T081 | 0.1 | 0.0005 | 5 mM S.C buffer, pH 5.5 | 109.5 |

In the test for the activity evaluation of the botulinum toxin through the animal potency test, 80 to 125% could be accepted as a suitable range. This is a phenomenon caused by variation in the animal potency test, and thus, the degree is significantly large as compared to general test methods. As shown in Table 4 above, it was confirmed that the titer of the botulinum toxin was 114.4%, which was stable, even when a very small amount of polysorbate 20, for example, a trace amount of 0.00075% (w/v) was used.

Example 5: Evaluation of Titer and Stability According to Concentration of L-Alanine In order to investigate the effect of the content of L-alanine on the potency of the botulinum toxin, the animal potency screening was conducted by changing the contents of L-alanine. In order to confirm the effect of L-alanine on the potency synergistic action of polysorbate 20 and the effect of L-alanine on interaction with sodium citrate buffer and stability, liquid injections were prepared with comprising 5 mM sodium citrate buffer and 0.001% polysorbate 20. L-alanine was used at concentrations of 0.1%, 0.02% and 0.05%, and the stability under stress conditions between 0.1% and 0.02% was compared and evaluated.

In the evaluation of the stability under stress conditions, the stress conditions were determined to 40° C. and 75% RH according to KFDA's notification, or to 37° C. in order to compare and evaluate the potency reduction aspect in consideration of thermal stability of the botulinum toxin type A and the animal potency test schedule. Hereinafter, all evaluations of stability under stress conditions were performed using the same method.

TABLE 5

Results of measuring animal potency and stability according to concentration of L-alanine

| Batch No. | L-alanine (w/v %) | polysorbate 20 (w/v %) | Buffer | Animal Titer (%) | 1 week1 s under stress conditions | 3 weeks under stress conditions |
|---|---|---|---|---|---|---|
| NBTS-50-T084 | 0.1 | 0.001 | 5 mM S.C buffer pH 5.5 | 103.5 | 103.8 | 89.4 |
| NBTS-50-T082 | 0.05 | 0.001 | 5 mM S.C buffer pH 5.5 | 104.4 | N/A | |
| NBTS-50-T083 | 0.02 | 0.001 | 5 mM S.C buffer pH 5.5 | 110.1 | 84.7 | 74.4 |

It could be confirmed that the higher the content of L-alanine, the higher the stability under stress conditions, and a synergistic action of the titer of polysorbate 20 was also partially suppressed. It was anticipated that L-alanine affected a critical micelle concentration of polysorbate 20, and it was confirmed that the combination with 0.1% L-alanine had only 14% activity reduction for 3 weeks under stress conditions. In view of the above results, the stability was particularly excellent when the concentration of L-alanine was 0.1%.

Example 6: Evaluation of Activity and Stability of Botulinum Toxin Type A by Buffer The buffer of the liquid composition was selected in consideration of the isoelectric point of the botulinum toxin type A. The sodium citrate buffer and sodium chloride that have a buffering capacity below pH 6.0, an isoelectric point of the botulinum toxin and that are the most commonly used in products for muscle administration, thereby confirming safety, were determined as a primary buffer of the formulation. In all of the present experiments, the sodium citrate buffer was prepared by comprising 0.9% (w/v) sodium chloride as an isotonic agent unless otherwise noted.

The botulinum toxin type A preparation was prepared by combining (i) L-alanine or methyl cellulose and (ii) polysorbate 20 with any one of (iii) two buffers, sodium citrate buffer (pH 5.5) and 0.9% (w/v) sodium chloride. The types and concentrations of excipients added to *Clostridium botulinum* toxin type A are summarized in Table 6 below.

After the buffer was prepared, L-alanine, methyl cellulose and polysorbate 20 were added to correspond to each concentration, thereby preparing an excipient solution. Then, the botulinum toxin was added to have a concentration of 40 U/ml.

TABLE 6

Results of measuring stability on botulinum toxin Type A according to types of buffers

| Batch No. | L-alanine (w/v %) | Methyl Cellulose (w/v %) | Polysorbate 20 (w/v %) | Buffer | Animal Titer (%) | 1 week1 s under stress conditions | 2 weeks under stress conditions |
|---|---|---|---|---|---|---|---|
| NBTS-50-T068 | 0.1 | | 0.001 | 0.9% NaCl | 116 | 96 | 72.8 |
| NBTS-50-T070 | | 0.00125 | 0.001 | 0.9% NaCl | 93.1 | 56.5 | N/A |
| NBTS-50-T076 | 0.1 | | 0.001 | 5 mM S.C buffer (pH 5.5), 0.9% NaCl | 111.9 | 92.9 | 73 |
| NBTS-50-T077 | | 0.00125 | 0.001 | 5 mM S.C buffer (pH 5.5), 0.9% NaCl | 128.6 | 86.7 | 86.7 |

As experimental results, as shown in Table 6, when the 0.9% (w/v) sodium chloride buffer was used, the combination of methyl cellulose and polysorbate 20 showed very low stability under stress conditions. On the other hand, the combination of L-alanine and polysorbate 20 showed activity reduction lower than that of the combination of methyl cellulose and polysorbate 20 at 1 week under stress conditions as compared to 0 week.

Meanwhile, when the sodium citrate buffer was used, the stability of the combination of methyl cellulose and polysorbate 20 was sufficiently increased, and the stability was maintained between 1 week and 2 weeks under stress conditions.

That is, it could be confirmed that when the sodium citrate buffer was used, maintainability of stability was improved. This is because the stability of the botulinum toxin could be maintained at pH 6.0 or less and phenomenon such as oxidation occurring in environments such as stress conditions, etc., could be alleviated by the function of the sodium citrate buffer.

TABLE 7

Results of measuring animal potency and stability through animal potency ($2^{nd}$ test) according to concentration of sodium citrate buffer (pH 5.5)

| Batch No. | L-alanine (%) | polysorbate 20 (%) | S.C Buffer (pH 5.5), 0.9% NaCl | Animal potency (%) | 1 week1 s under stress conditions | 2 weeks under stress conditions |
|---|---|---|---|---|---|---|
| NBTS-50-T076 | 0.1 | 0.001 | 5 mM | 111.9 | 92.9 | 73 |
| NBTS-50-T084 | 0.1 | 0.001 | 10 mM | 103.5 | 103.8 | 82.1 |
| NBTS-50-T085 | 0.1 | 0.001 | 20 mM | 106.6 | 97.5 | 89.4 |

In addition, in the secondary test results, it was confirmed that 10 mM or more sodium citrate buffer partly contributed to maintenance of stability under stress conditions. In particular, the stability was the highest when 20 mM sodium citrate buffer was used.

INDUSTRIAL APPLICABILITY

The liquid composition of the botulinum toxin according to the present disclosure is which is ready-to-use without performing a reconstitution process, and thus, it is possible to improve user's convenience, and reduce a deviation of botulinum toxin activity due to dilution errors in the reconstitution process, etc. Further, the liquid composition according to the present disclosure efficiently prevents the botulinum toxin from aggregating even at a low botulinum toxin concentration to thereby have extremely excellent storage stability, and efficiently prevents adsorption of the botulinum toxin to a container, thereby constantly maintaining an activity of the botulinum toxin for each batch or for each liquid vial.

Although specific embodiments of the present disclosure are described in detail, it will be apparent to those skilled in the art that the specific description is merely desirable exemplary embodiment and should not be construed as limiting the scope of the present disclosure. Therefore, the substantial scope of the present disclosure is defined by the accompanying claims and equivalent thereof.

The invention claimed is:

1. A liquid composition comprising (i) a botulinum toxin, (ii) L-alanine or methyl cellulose, (iii) a non-ionic surfactant, and (iv) a buffer,
wherein the liquid composition comprises 0.01 to 0.2% w/v L-alanine based on the total content of the composition, or 0.00125 to 0.05% w/v methyl cellulose based on the total content of the composition,
wherein the non-ionic surfactant is polysorbate 20 and the liquid composition comprises 0.0005 to 0.1% w/v polysorbate 20 based on the total content of the composition, and
wherein the buffer is NaCl buffer or sodium citrate buffer.

2. The liquid composition according to claim 1, wherein the botulinum toxin is a botulinum toxin type A.

3. The liquid composition according to claim 1, comprising 5 to 35 mM sodium citrate as a buffer based on the total content of the composition.

4. The liquid composition according to claim 1, further comprising an isotonic agent and the isotonic agent is comprised with a content of 0.7 to 0.95% w/v based on the total content of the composition.

5. The liquid composition according to claim 1, wherein the composition is ready-to-use for injection.

6. A method for stabilizing a botulinum toxin using a liquid composition according to claim 1.

7. The method according to claim 6, wherein the liquid composition further comprises an isotonic agent.

\* \* \* \* \*

UNITED STATES PATENT AND TRADEMARK OFFICE
CERTIFICATE OF CORRECTION

PATENT NO. : 11,185,503 B2
APPLICATION NO. : 16/477889
DATED : November 30, 2021
INVENTOR(S) : Hyeona Yim et al.

Page 1 of 1

It is certified that error appears in the above-identified patent and that said Letters Patent is hereby corrected as shown below:

In the Specification

Column 6, Line 6, "polysorbate 20 or polysorbate has a content" should be -- polysorbate 20 or polysorbate 80 has a content --.

Column 9, Line 59, "polysorbate into the liquid composition" should be -- polysorbate 20 into the liquid composition --.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*